US012808444B2

(12) United States Patent
Schlitt

(10) Patent No.: US 12,808,444 B2
(45) Date of Patent: Nov. 24, 2026

(54) NON-RETURN VALVE, DRIP CHAMBER, PORT FOR NEEDLE-FREE METERING OF A LIQUID, BACK-FLOW BARRIER, INFUSION OR TRANSFUSION SYSTEM AND METHOD FOR PRODUCING A NON-RETURN VALVE

(71) Applicant: B. Braun Melsungen AG, Melsungen (DE)

(72) Inventor: Christof Schlitt, Frielendorf (DE)

(73) Assignee: Braun Melsungen AG, Melsungen (DE)

( * ) Notice: Subject to any disclaimer, the term of this patent is extended or adjusted under 35 U.S.C. 154(b) by 0 days.

(21) Appl. No.: 19/052,457

(22) Filed: Feb. 13, 2025

(65) Prior Publication Data

US 2025/0180132 A1 Jun. 5, 2025

Related U.S. Application Data

(62) Division of application No. 17/795,580, filed as application No. PCT/EP2021/052809 on Feb. 5, 2021, now Pat. No. 12,259,048.

(30) Foreign Application Priority Data

Feb. 6, 2020 (DE) ..................... 10 2020 201 483.3

(51) Int. Cl.
*F16K 15/14* (2006.01)
*A61M 39/24* (2006.01)

(52) U.S. Cl.
CPC ........... *F16K 15/147* (2013.01); *A61M 39/24* (2013.01)

(58) Field of Classification Search
CPC .............................. F16K 15/147; A61M 39/24
See application file for complete search history.

(56) References Cited

U.S. PATENT DOCUMENTS

| | | | | |
|---|---|---|---|---|
| 4,778,461 | A * | 10/1988 | Pietsch | A61L 33/0005 623/2.19 |
| 5,305,795 | A | 4/1994 | Forberg | |
| 6,165,168 | A | 12/2000 | Russo | |
| 6,537,258 | B1 | 3/2003 | Guala | |
| 9,097,355 | B2 | 8/2015 | Keller | |
| 11,092,254 | B1 | 8/2021 | Rueda Calvet | |
| 2003/0171721 | A1 | 9/2003 | Enomoto et al. | |

(Continued)

FOREIGN PATENT DOCUMENTS

| | | |
|---|---|---|
| DE | 8226186 U1 | 12/1982 |
| DE | 3518841 C2 | 7/1993 |

(Continued)

OTHER PUBLICATIONS

Examination Report received in Indian Application No. 202217043528 dated Jan. 11, 2023, with translation, 7 pages.

(Continued)

*Primary Examiner* — P. Macade Nichols
(74) *Attorney, Agent, or Firm* — Christopher A. Rothe; CM Law

(57) ABSTRACT

A method of manufacturing a check valve includes the step of liquid injection molding an elastic material to form a valve body that is pot-shaped, so that the valve body has a lateral wall, a bottom wall, and an opening opposite the bottom wall. The method can also include the step of cutting the elastic material along a cut.

19 Claims, 2 Drawing Sheets

(56) References Cited

U.S. PATENT DOCUMENTS

| | | | | |
|---|---|---|---|---|
| 2006/0253084 | A1 | 11/2006 | Nordgren | |
| 2016/0030730 | A1* | 2/2016 | Mosler | A61M 39/24 604/247 |
| 2020/0189969 | A1 | 6/2020 | Sieutat et al. | |

FOREIGN PATENT DOCUMENTS

| | | | |
|---|---|---|---|
| DE | 102016114789 | A1 | 2/2018 |
| DE | 202018003825 | U1 | 11/2018 |
| EP | 0515597 | B1 | 8/1996 |
| EP | 1892034 | A1 | 2/2008 |
| GB | 2387333 | A | 10/2003 |
| WO | 0057941 | A1 | 10/2000 |
| WO | 2006118748 | A1 | 11/2006 |

OTHER PUBLICATIONS

Search Report received in International Application No. PCT/EP2021/052809 dated May 12, 2021, with translation, 6 pages.
Written Opinion received in International Application No. PCT/EP2021/052809 dated May 12, 2021, with translation, 12 pages.
Office Action received in Brazilian Application No. BR112022015196-9 dated Mar. 18, 2025, with translation, 6 pages.

* cited by examiner

Section A-A

NON-RETURN VALVE, DRIP CHAMBER, PORT FOR NEEDLE-FREE METERING OF A LIQUID, BACK-FLOW BARRIER, INFUSION OR TRANSFUSION SYSTEM AND METHOD FOR PRODUCING A NON-RETURN VALVE

CROSS-REFERENCE TO RELATED APPLICATIONS

This application is a divisional of U.S. application Ser. No. 17/795,580, filed Jul. 27, 2022, which is the United States national stage entry of International Application No. PCT/EP2021/052809, filed Feb. 5, 2021, and claims priority to German Application No. 10 2020 201 483.3, filed Feb. 6, 2020. The contents of U.S. application Ser. No. 17/795,580, International Application No. PCT/EP2021/052809 and German Application No. 10 2020 201 483.3 are incorporated by reference herein in their entireties.

FIELD

The invention relates to a check valve, a drip chamber for an infusion system or transfusion system, a port for the needleless admixture of a fluid into an infusion system or transfusion system, a backflow preventer for the fluid line of an infusion system or transfusion system, an infusion system or transfusion system comprising the check valve, and a method of manufacturing a check valve.

BACKGROUND

In medical technology, check valves play an important role for various therapeutic fields and for various drug administration methods. For example, in infusion or pain therapy, check valves control the ventilation of drip chambers, the direction of flow of fluids or serve as a port (i.e. access) for the needleless admixture of fluids. In particular if the medical device is designed for single use, low manufacturing costs of the various components of the product are important such that it can be economically placed on the market.

Various check valves are commercially available and described in the literature.

For use in medical technology, it is necessary that the materials from which the check valves are made are biocompatible. Furthermore, they must be compatible with the fluids with which they come into contact during use. In addition, they must have the required mechanical properties, such as sufficient mechanical strength.

Check valves made of elastic and biocompatible materials can have such a suitability. Different versions are known. For example, EP 0 515 597 B1 describes a disc valve which has a certain pre-tension due to its design and thus blocks the passage of fluid in one flow direction. But if a certain pressure, triggered by a flowing fluid, is present from the opposite direction, the valve disc lifts off and releases the passage. However, the manufacture of disc valves is complex and therefore expensive. In particular, the manufacturing tolerances imposed on the valve disc and the valve seat in the components in which the valve is installed as well as the assembly tolerances of these components relative to each other are low, which makes the manufacture of the parts uneconomical. Because of to the high demands imposed on the tolerances, disc valves tend to let fluids through in the blocking direction even in the case of minor dimensional deviations, which cannot be ruled out with certainty even in the case of careful production. Such valves are therefore not sufficiently safe. Furthermore, so-called duckbill valves are known, which have the shape of a tube that tapers linearly along the transverse axis at one end such that only a gap remains. If pressure is exerted on the gap by fluid flows through the tube, the gap opens. When fluid flows in the opposite direction, the gap should be closed. The manufacture of duckbill valves is also complex and expensive. Duckbill valves also have very high leakage rates because the gap is always slightly open and is not closed at low pressures in the blocking direction. In addition, they operate very inconstantly with regard to the opening pressures.

Furthermore, DE 82 26 186 U1 describes a pot valve made of an elastic material in which the pot-shaped valve body is incised on one side close to the pot base, i.e. it has a slit, such that the pot base can lift off from the rest of the valve body to a certain extent. Thus, the passage is opened by the pressure of a fluid flowing through the pot, but closed when the flow is in the opposite direction. The function of the pot valve requires that it is made of an elastic material.

The elastic material is required to ensure that the incised slit does not close again during the manufacture of the valve and the medical device and during the life cycle of the medical device until its expiry date, for example by chemicals such as ethylene oxide used for sterilisation purposes or by introduced energy in the form of heat or other radiation, for example high-energy radiation applied for sterilisation purposes (gamma radiation etc.). The property that the incised slit closes again at least partially is referred to as “selfhealing” or “self-healing” of the material. Partial or complete closure of the slit is understood to mean that the surfaces of the cut reduce in size or entirely disappear because the material on one cut surface bonds with the material on the other cut surface in that the material on one cut surface and the material on the other cut surface adhere to each other or penetrate each other. Such self-healing results in the check valve not working reliably, or at least not for a sufficiently long time.

In the case of typical applications of a component made of an elastic material, the self-healing tendency of the elastic material is not a problem; in some circumstances, self-healing is even conventionally desired. This may be because the component is not exposed to conditions that promote self-healing, i.e. is not exposed to such chemicals or such radiation. Therefore, the self-healing tendency of a resilient material is usually not considered important. Notwithstanding this, the inventor has recognised that self-healing may be disadvantageous in some circumstances, particularly in the case of check valves for medical applications which have an incised elastic valve body.

Conventional pot valves are made of materials that do not satisfactorily meet these requirements, i.e. they exhibit self-healing to an unacceptable degree, and/or they are manufactured using complex and therefore expensive manufacturing processes, and/or they are manufactured using slow and therefore expensive manufacturing processes, and/or they have a low elongation at break, which means that the bottom of the pot can easily break off at the location of the cut slit during further processing of the valve. Conventional pot valves are made, for example, of HCR silicone. The abbreviation “HCR” stands for “High Consistency Rubber”. To produce a component from HCR silicone, a paste-like or dough-like mass which in addition to the polymer material and any fillers and additives includes a vulcaniser is pressed into a mould and cross-linked in the mould at high temperature. This process is also known as “HCR pressing”. HCR silicones are not only laborious in processing, but also result in components with low elongation at break.

SUMMARY

It is therefore an objective of the invention to provide an improved check valve, in particular an improved check valve for a medical device. In particular, it is an objective of the invention to provide a check valve which has a low leakage rate and operates reliably over a long life cycle and which is nevertheless manufactured in a simple and economically favourable manner. It is also an objective of the invention to provide improved medical devices comprising one or more check valves and components for such medical devices.

These objectives are solved by the check valve according to claim 1, the drip chamber according to claim 10, the port according to claim 11, the backflow preventer according to claim 12, the infusion system or transfusion system according to claim 13, and the method according to claim 14. Herein, the features set out in the dependent claims and the following description may also be used for configuring the subject-matter of another claim category or of a further patent claim of the same category.

The check valve according to the invention is a check valve comprising a pot-shaped valve body. The valve body has a lateral wall, a bottom wall, and an opening opposite to the bottom wall. The valve body comprises an elastic material. The elastic material is incised along a cut, thereby having a slit. The elastic material comprises a material processed by liquid injection moulding.

For example, the invention may provide a check valve that has low leakage rates. It may operate reliably at different pressure conditions and prevent a flow of a fluid against the blocking direction. It may retain these properties over a long life cycle. At the same time, it is comparatively simple in terms of manufacturing technology to comply with the requirements regarding tolerances.

For example, the invention may provide a check valve that is robust during further processing in subsequent processes, storage, and transport and is suitable for medical use. Furthermore, it may be possible to mass produce the check valve.

Furthermore, the check valve is manufactured by means of an economically advantageous process, which is particularly advantageous for mass production. It was neither known nor foreseeable in the prior art that a check valve with such advantageous properties could be manufactured in such an economically advantageous manner.

The drip chamber according to the invention is a drip chamber for an infusion system or transfusion system. The drip chamber comprises a venting valve. The venting valve is a check valve according to the invention. Thus, a drip chamber is provided which has the advantages of the check valve according to the invention.

The infusion system or transfusion system according to an alternative of the invention is an infusion system or transfusion system with at least one drip chamber, wherein a drip chamber according to the invention serves as the drip chamber. Thus, an infusion or transfusion system is provided which has the advantages of the check valve according to the invention.

In the context of this disclosure, an infusion or transfusion system is understood to be a system that can be used to administer a medical infusion or perform a medical transfusion. In particular, it may be an infusion set (also referred to as an "infusion device"). An infusion set comprises an infusion tube and a connector by which the infusion tube can be connected to a container containing the fluid to be administered to a patient. A drip chamber is optionally arranged between the connector and the infusion tube. The container may be, for example, an infusion bottle, an infusion bag, a blood bag, etc. The infusion tube has a connector for a patient access (e.g. venous cannula or venous catheter). The patient access may optionally be considered part of the infusion set. The infusion set may optionally comprise further components, for example a flow controller for controlling the flow rate of the fluid such as a roller clamp.

The port according to the invention is a port for needleless admixture of a fluid into an infusion or transfusion system, wherein a check valve according to the invention serves as the port. Thus, a port is provided which has the advantages of the check valve according to the invention.

The infusion or transfusion system according to an alternative of the invention is an infusion or transfusion system with at least one port for the needleless admixture of a fluid, wherein a check valve according to the invention serves as the port. This provides an infusion or transfusion system having the advantages of the check valve according to the invention.

The backflow preventer according to the invention is a backflow preventer for the fluid line of an infusion or transfusion system, wherein a check valve according to the invention serves as the backflow preventer. This provides a backflow preventer which has the advantages of the check valve according to the invention.

The infusion system or transfusion system according to an alternative of the invention is an infusion or transfusion system with at least one backflow preventer for preventing a flow of a fluid in a fluid line in one flow direction, wherein a backflow preventer according to the invention serves as the backflow preventer. This provides an infusion or transfusion system having the advantages of the check valve according to the invention.

The method according to the invention is a method of manufacturing a check valve comprising a pot-shaped valve body having a lateral wall, a bottom wall, and an opening opposite to the bottom wall, the method comprising the following steps:

(A) providing an elastic material, (B) liquid injection moulding an elastic material to produce the valve body, (C) cutting the elastic material along a cut to create a slit in the valve body.

The elastic material may be provided, for example, in the form of components from the mixture of which the elastic material is formed.

Further features and expediencies of the invention are described below by means of exemplary embodiments of the check valve according to the invention with reference to the attached drawings. The installation of these check valves in corresponding medical devices results in embodiments of these medical devices according to the invention.

BRIEF DESCRIPTION OF THE DRAWING FIGURES

DETAILED DESCRIPTION

Figure 1:
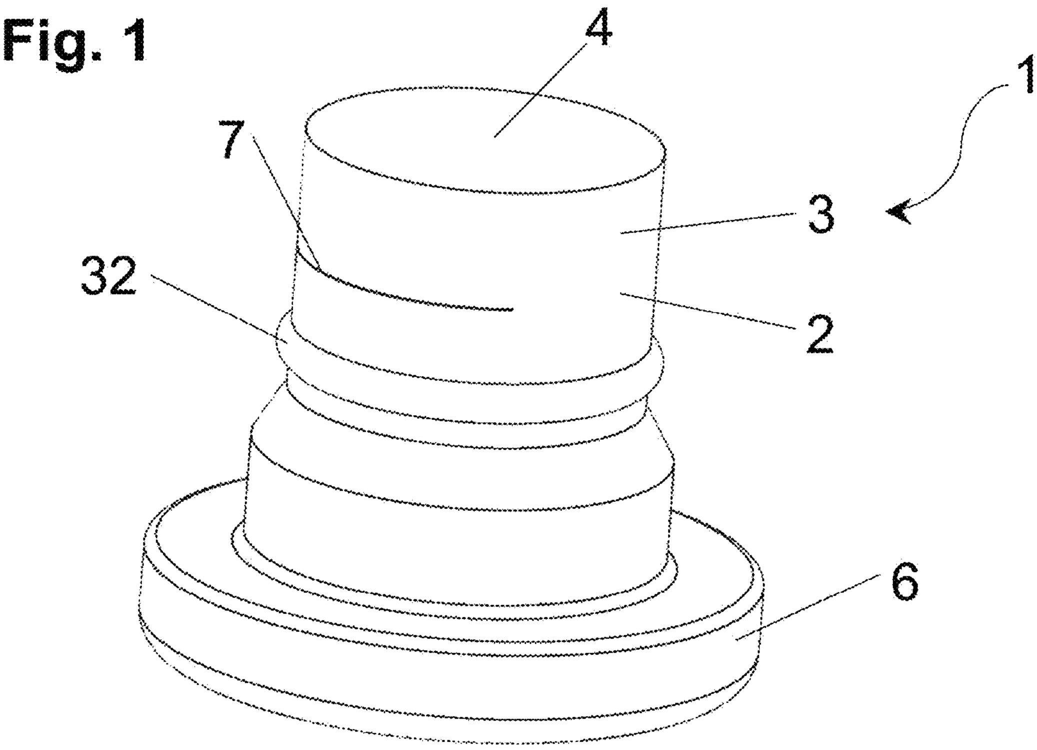
FIG. 1 shows an isometric view of the check valve according to a first embodiment of the invention.
Figure 2:
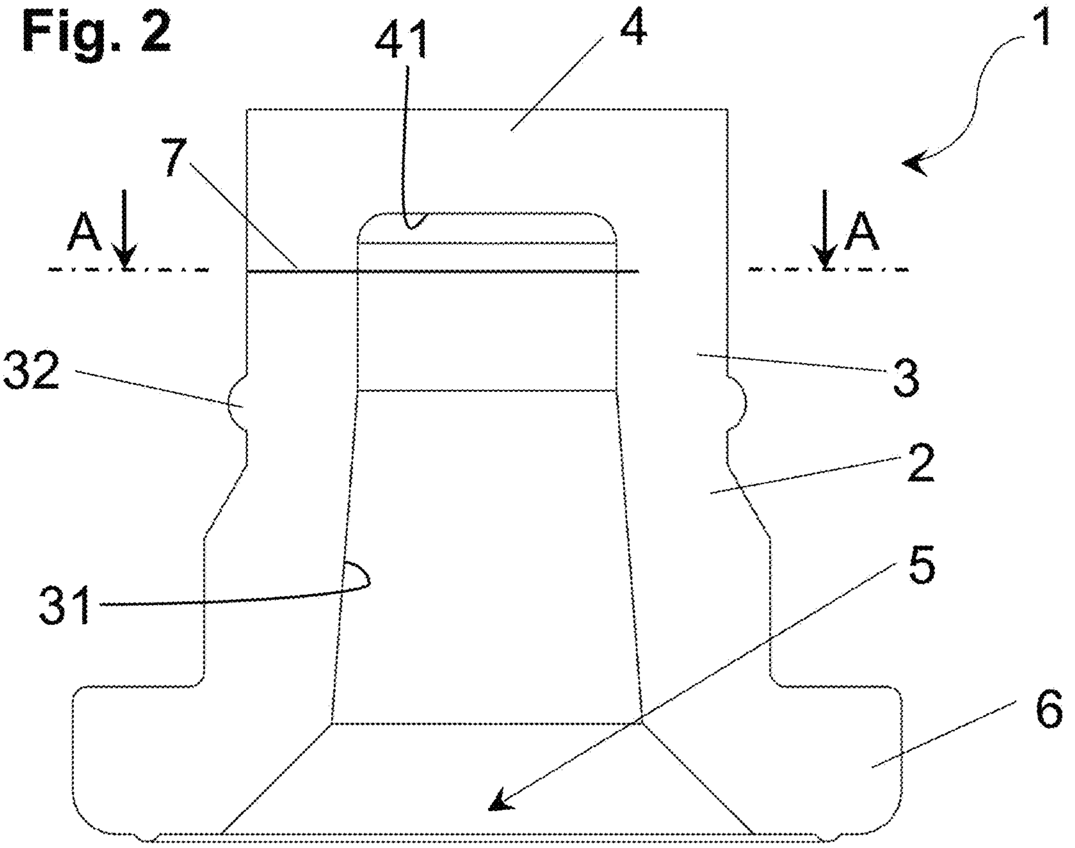
FIG. 2 shows a sectional view of the check valve according to the invention according to the first embodiment.
Figure 3:
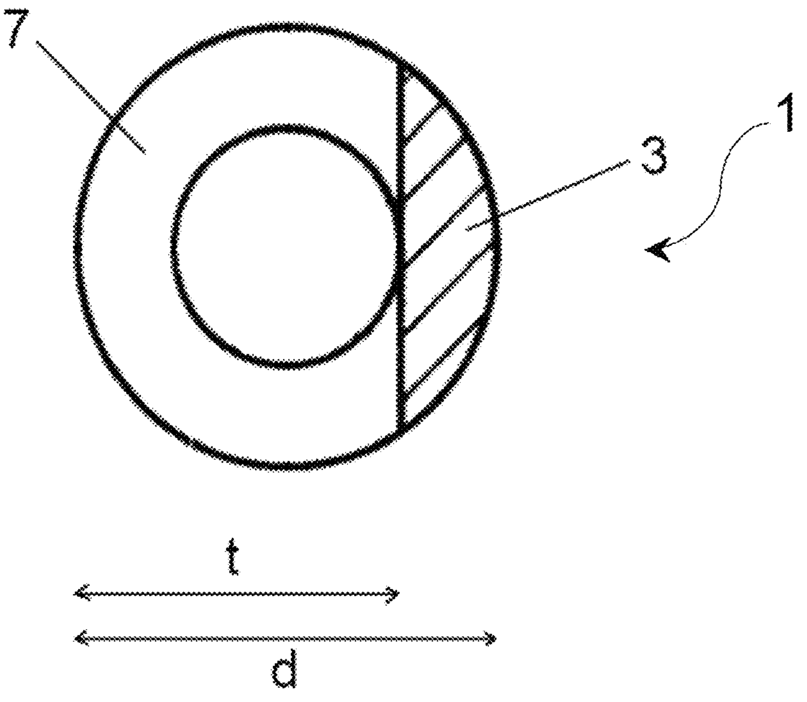
FIG. 3 shows a further sectional view of the check valve according to the invention according to the first embodiment.

FIGS. 1 to 3 show various views of the check valve 1 according to the invention. The check valve 1 comprises a pot-shaped valve body 2, i.e. the valve body 2 is in the form of a hollow body closed on one side. The valve body 2 has a lateral wall 3, which forms the skirt of the hollow body, and a bottom wall 4, which forms the closed bottom of the hollow body. On the side opposite the bottom wall 4, the valve body 2 has an opening 5.

A flange 6 is attached around the opening 5 on the side opposite the bottom wall 4. The flange 6 serves to fix the check valve 1 in a component, in particular in a component of a medical device. The flange 6 is integrally attached to the lateral wall 3. In alternative embodiments of the invention that are not shown in the drawings, the flange 6 is not formed integrally with the rest of the valve body 2 but as a separate element and connected to the lateral wall 3. In further alternative embodiments of the invention, also not shown in the drawings, the valve body 2 does not comprise a flange 6 and is intended to be fixed in a component by attachment means other than a flange, for example by gluing and/or welding and/or a press connection. Since the flange 6 provides a secure and simple means of fastening the check valve 1, it is preferred that the check valve 1 has a flange 6. With regard to the manufacture as well as the properties and function of the integrally moulded flange 6, the liquid injection moulding process is particularly advantageous. It is possible to realise the flange 6 by means of the liquid injection moulding process without any additional processing step. In the case of a manufacturing process based on material removal, the flange 6 would have to be created in a separate step, e.g. by cutting its shape out of the valve body 2.

In the orientation of the check valve 1 shown in FIGS. 1 and 2, in which the bottom wall 4 is at the top, the lateral wall 3 is cut through on one side below the inner surface 41 of the bottom wall 4, i.e. it has a cut 7. The material of the lateral wall 3 is bisected along the cut 7.

FIG. 3 shows a section in the plane A-A, which is indicated in FIG. 2 and which is perpendicular to the longitudinal direction of the check valve 1 from the opening 5 to the bottom wall 4. The cut 7 lies in the plane A-A.

Accordingly, in the present embodiment, the cut 7 lies in a plane, i.e. the cut surfaces are flat. In alternative embodiments that are not shown in the drawings, the cut 7 does not lie in a plane, i.e. the cut surfaces are not flat, but, for example, curved.

In the present embodiment, the cut 7 is parallel to the inner surface 41 of the bottom wall 4. In alternative embodiments that are not shown in the drawings, the cut 7 is not parallel to the inner surface 41 of the bottom wall 4, but inclined to the inner surface 41 of the bottom wall. In this case, it is preferred that the cut 7 is arranged in the lateral wall 3 in such a way that it has an inclination to the inner surface 41 of the bottom wall 4 which is at most 10°, more preferably at most 5°, even more preferably at most 2°, and in particular preferably at most 1°.

In the present embodiment, the cut 7 has a distance from the inner surface 41 of the bottom wall 4 which is approximately 25% of the outer diameter d of the lateral wall 3 in the region of the cut 7. In alternative embodiments that are not shown in the drawings, the cut 7 has a greater or lesser distance from the bottom wall 4.

The depth t of the cut 7 in the present embodiment is 75% of the outer diameter d of the lateral wall 3 in the plane A-A, i.e. the lateral wall 3 is cut along 75% of the outer diameter and not cut along the remaining 25%. The non-cut area of the lateral wall 3 is shown hatched in FIG. 3. In alternative embodiments that are not shown in the drawings, the cut 7 is deeper or less deep than 75% of the outer diameter d of the lateral wall 3. In this case, it is preferred that the depth t of the cut is at least 50%, more preferably at least 60%, even more preferably at least 70%, and in particular preferably at least 72.5% of the outer diameter d of the lateral wall 3 in the region of the cut 7. Herein, it is further preferred that the depth t of the cut is at most 90%, more preferably at most 85%, even more preferably at most 77.5% of the outer diameter d of the lateral wall 3 in the region of the cut 7. In all cases, the depth t of the cut 7 is to be selected such that the check valve 1 opens reliably at the desired opening pressure but not at lower pressures, in that the lateral wall opens in the region of the slit and allows a fluid to flow through in the direction of passage.

In the present embodiment, the inner surface 31 of the lateral wall 3 tapers in the direction from the opening to the bottom wall 4. In alternative embodiments that are not shown in the drawings, the inner surface 31 of the lateral wall 3 is circular cylindrical.

The lateral wall 3 comprises a circumferential protrusion 32 on its outer surface. This bead 32 offers advantages in production processes, for example because it can improve the fastening of the check valve in another component that has a corresponding groove. In addition, the protrusion 32 can improve the seal against that component even if the latter does not have a groove. In alternative embodiments that are not shown in the drawings, the lateral wall 3 has a circumferential groove as an alternative or in addition to this protrusion. The protrusion or groove can also be arranged on the inner surface of the lateral wall 3. The protrusion or groove does not necessarily have to be circumferential, i.e. run along the entire circumference of the lateral wall 3. There may also be several protrusions and/or grooves.

In the present embodiment, apart from the cut 7, the check valve 1 has a rotationally symmetrical design. This is not necessary for the function of the check valve 1, such that other shapes are also possible. However, a rotationally symmetrical shape is in many cases advantageous from a manufacturing point of view and/or better adapted to the spatial conditions of the component in which the check valve 1 is to be installed than, for example, a shape with an elliptical cross-section.

In the present embodiment, the valve body 2 consists of an elastic material. In alternative embodiments, the valve body is not entirely made of an elastic material but comprises further components made of a different material in addition to the elastic material. For example, a flange 6 made of a non-elastic material may be connected to the rest of the valve body made of an elastic material.

In any case, the valve body 2 comprises an elastic material which has been processed by liquid injection moulding. By means of the invention, it is thus possible to manufacture a check valve 1 with appropriate properties and to use the advantages of liquid injection moulding, in particular an economically advantageous process control and/or simple automation and/or unproblematic compliance with the required manufacturing tolerances.

In liquid injection moulding, a liquid polymer material is used which is usually produced from various components by mixing. The different components may be, for example, a base and a catalyst-containing component. When these components are mixed with each other, a polymerisation reaction and/or a cross-linking reaction starts. Initially, the mixture is liquid and can be processed by liquid injection moulding. For this, the mixture is dosed into the moulds. The material cures in the mould and is ejected from the mould when the curing process is sufficiently complete. Due to the liquid processing, liquid injection moulding is less complex in terms of equipment than, for example, HCR pressing, where high pressures and high temperatures have to be applied. In addition, processing by means of HCR pressing is slow.

In preferred embodiments of the invention, the material processed by liquid injection moulding is a silicone, in particular a silicone rubber. In other words, a liquid silicone rubber ("LSR" for short) is used for liquid injection moulding. The elastic material of the check valve 1 is then a cured and/or cross-linked liquid silicone rubber. This designation does not mean that the cured and/or cross-linked material is still liquid, but that it has been processed in liquid form and therefore has the corresponding properties.

In alternative embodiments, the material processed by liquid injection moulding is a polyolefin. In this case, cross-linkable polyolefin plastisols (also referred to as "PO plastisols") are used for liquid injection moulding.

It is preferred that the elastic material has a low self-healing rate, in particular a low self-healing rate when energy is introduced into the material, for example in the form of heat or other radiation, for example high-energy radiation (gamma radiation, etc.) introduced for sterilisation purposes.

Herein, the self-healing rate of an elastic material is defined as the proportion (in percent) of a number of test specimens provided with a slit, whose slit surfaces have reduced in size to a maximum of 10% after a test duration due to partial closure of the slit. At least ten flat test specimens with a thickness of 2 mm serve as test specimens. The cut runs in the direction of the thickness of the test specimen. The length of the cut is 5 mm. The test duration is 14 days. During the test period, the test specimens are exposed to a temperature of 50° C.

In particularly preferred embodiments of the invention, the selected liquid silicone rubber is a liquid silicone rubber with advantageous chemical and physical properties, in particular a liquid silicone rubber that leads to an elastic material with a low self-healing rate and/or has a low content of volatile substances and/or meets the requirements of the authorities responsible for the approval of medical devices.

It is further preferred to add an additive to the material to be processed by liquid injection moulding before or during processing by liquid injection moulding to further improve the properties of the elastic material. The additive may be added to any of the components of the liquid injection mouldable material, or it may be added to the liquid injection mouldable material as an additional component. For example, a suitable additive may be added to reduce the self-healing rate.

Preferably, the additive is added in a dosage of at least 1 wt % and/or at most 20 wt %. The weight percentages (wt %) result from the mass of the additive in relation to the sum of the mass of the material to be processed by liquid injection moulding and the mass of the additive. A dosage of at least 2% by weight and at most 20% by weight is more preferred, and most preferably at least 2% by weight and at most 10% by weight. This makes it possible, for example, to achieve an advantageously low self-healing rate with simultaneously advantageous elastic properties.

The additive is preferably a filler. By a "filler" is meant an additive which does not dissolve or does not dissolve to any significant extent in the elastic matrix material.

More preferably, the additive is a filler which contains or consists of filler particles. In this case, the filler particles dissolve in the elastic matrix material neither during processing by liquid injection moulding nor afterwards and are therefore still present in the check valve (1) according to the invention as particles dispersed or embedded in the matrix material, even after a long storage time. Such a filler may be added to the elastic material, for example, in the form of a powder. The powder is preferably a fine powder, in particular of a size in the micrometre range.

For example, the filler may be one of the following substances or a mixture of one of the following substances or a mixture of several of the following substances:

- glass, e.g. in the form of glass fibres, glass beads and broken glass
- mineral fillers, e.g. silicate or calcium carbonate powder
- carbon fibres
- carbon blacks.

Herein, it is preferred that the additive comprises a mineral substance, wherein it is further preferred that the mineral substance is a silicate. In particular, the mineral filler may be talcum powder.

With suitable additives, in particular mineral fillers and among them preferably silicates and particularly preferably talcum, it may be possible to improve the material properties of the material processed by liquid injection moulding. An improvement of the material properties is primarily understood as an increase in the roughness of the cut surfaces of a cut in the material. Rough cut surfaces do not lie flat against each other, i.e. they are spaced apart from each other at least at certain points. This reduces the self-healing tendency.

An alternative measure to reduce self-healing may be the use of lubricants as process-accompanying auxiliary materials. Lubricants form a lubricating film on the cut surfaces or they prevent the two opposing cut surfaces ("slit edges") from touching each other directly. To achieve this, either a liquid or particulate lubricant is applied to the cut surfaces when the valve body is slit, or an appropriate oil or grease is already added to the starting material which then "sweats out", i.e. gradually escapes, over the duration of storage and use. This alternative measure may not only be relatively expensive to implement. The lubricants may also contaminate the production equipment, for example because the lubricants stick to tools. In particular, problems result when escaping lubricant leads to contamination of the equipment as well as tools, operating facilities, packaging materials, etc. during intermediate storage of the check valves and during installation in equipment (e.g. in medical devices). This results in additional effort due to cleaning measures or even in a deterioration of the product quality. Leaking excipients are particularly problematic in the medical field. For example, if these auxiliary substances get into an infusion solution flowing through the check valve, they subsequently enter the bloodstream of a patient.

Particularly in view of this, it is preferred, instead of this alternative measure, to add a filler, in particular a mineral filler, to the material to be processed by liquid injection moulding before or during processing by liquid injection moulding as described above. In this way, silicone valves according to the invention can be manufactured quickly, cleanly and inexpensively, and at the same time the self-healing tendency is strongly suppressed.

While components manufactured by liquid injection moulding from elastic materials to which no fillers are added are usually transparent, the addition of fillers often results in opaque liquid injection products. Opacity does not lead to any limitation of the useful properties of the check valve according to the invention.

The choice of the liquid material from which the elastic material is manufactured by liquid injection moulding and/or the choice of additives added to this material is an important aspect of preferred embodiments, and may lead to particularly favourable material properties. In addition to biocompatibility and compatibility with the materials of the other components of a medical device, particularly favourable aspects include, for example, a hardness of at least 50 Shore A, a particularly low self-healing rate, and the possibility of producing, by cutting the elastic material, a cut 7 with cut surfaces having a sufficient roughness, in particular a roughness of at least Ra=0.15 μm.

In the method according to the invention for manufacturing a check valve, the step of cutting through the elastic material along a cut is preferably performed in such a way that the cut surfaces have a sufficient roughness, in particular a roughness of at least Ra=0.15 μm. This may be achieved, for example, by a suitable choice of cutting tool and/or cutting speed depending on the respective elastic material.

The addition of additives, in particular of particle-containing auxiliary materials, may contribute to an advantageous, material-related roughness of the cut surfaces, in particular a roughness of at least Ra=0.15 μm, or ensure that the cut surfaces have such a roughness. According to a non-limiting theory, this is due to the fact that particles occur in the area of the cut which at least partially protrude from the cut surfaces and thus result in an unevenness of the cut surfaces.

The invention claimed is:

1. A method of manufacturing a check valve, the method comprising the steps of:

liquid injection molding an elastic material to form a valve body that is pot-shaped, the valve body comprising a lateral wall, a bottom wall, and an opening opposite the bottom wall; and cutting the elastic material along a cut;

wherein the cut has cut surfaces having a roughness of at least Ra=0.15 μm.

2. The method according to claim 1, wherein the elastic material comprises a material processed by liquid injection molding using liquid silicone rubber.

3. The method according to claim 2, wherein the material processed by liquid injection molding has a self-healing rate of at most 50%.

4. The method according to claim 1, wherein an additive is added to the elastic material.

5. The method according to claim 4, wherein the additive is added to the elastic material before the step of liquid injection molding the elastic material to form the valve body.

6. The method according to claim 4, wherein the additive is added to the elastic material after the step of liquid injection molding the elastic material to form the valve body.

7. The method according to claim 4, wherein the additive is added to the elastic material during the step of cutting the elastic material along the cut.

8. The method according to claim 4, wherein a dosage of the additive, based on a total amount of the additive and the elastic material, is at least 1% by weight.

9. The method according to claim 4, wherein the additive is a filler.

10. The method according to claim 9, wherein the filler comprises at least one of a mineral substance or particles.

11. The method according to claim 9, wherein the filler comprises a silicate or talcum powder.

12. The method according to claim 4, wherein the additive comprises a functional filler that increases a roughness of a cut surface of the cut as compared to a material processed by liquid injection molding without the functional filler.

13. The method according to claim 1, wherein the lateral wall and the bottom wall are formed as one piece.

14. The method according to claim 1, further comprising the step of forming a protrusion and/or a groove on an outer surface of the lateral wall.

15. The method according to claim 1, further comprising the step of forming a protrusion and/or a groove on an inner surface of the lateral wall.

16. The method according to claim 1, wherein:

the lateral wall extends along an axis, and an inner surface of the lateral wall tapers inwardly along the axis towards the bottom wall.

17. The method according to claim 1, wherein the bottom wall tapers conically.

18. The method according to claim 1, further comprising the step of forming a flange around the opening.

19. The method according to claim 18, wherein the flange and the lateral wall are formed as a one piece body of unitary construction.

* * * * *